United States Patent
Muir et al.

(10) Patent No.: US 12,098,427 B2
(45) Date of Patent: Sep. 24, 2024

(54) GENETIC TESTING FOR INHERITED PERIPHERAL NEUROPATHY

(71) Applicant: Wisconsin Alumni Research Foundation, Madison, WI (US)

(72) Inventors: Peter Muir, Madison, WI (US);
Susannah Sample, Madison, WI (US);
John Svaren, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/946,613

(22) Filed: Sep. 16, 2022

(65) Prior Publication Data

US 2023/0014028 A1 Jan. 19, 2023

Related U.S. Application Data

(62) Division of application No. 16/745,608, filed on Jan. 17, 2020, now Pat. No. 11,473,146.

(60) Provisional application No. 62/794,750, filed on Jan. 21, 2019.

(51) Int. Cl.
*C12Q 1/6883* (2018.01)
(52) U.S. Cl.
CPC ..... *C12Q 1/6883* (2013.01); *C12Q 2600/156* (2013.01)
(58) Field of Classification Search
None
See application file for complete search history.

(56) References Cited

U.S. PATENT DOCUMENTS 10,858,708 B2  12/2020  Muir et al.
2016/0222451 A1  8/2016  Muir et al.

OTHER PUBLICATIONS

The Broad Institute, SNP BICF2P117167 on Chromosome 10, available via URL: <broadinstitute.org/files/shared/mammals/dog/snp2/snp_lists/chr10_allsnps.txt>, printed on Sep. 20, 2023 (Year: 2023).*
Dockerty, R. J. "A Multifactorial Genetic Approach to Improving Welfare in the Racing Greyhound" Dissertation Thesis. published 2017, available via URL: <livrepository.liverpool.ac.uk/3012340/1/200161464_Jan2016.pdf> (Year: 2017).*
Baird et al. "Genome-wide association study identifies genomic regions of association for cruciate ligament rupture in Newfoundland dogs," Stichting International Foundation for Animal Genetics. 2014. 45: 542-549.
Baker et al. "Genome-wide association analysis in dogs implicates 99 loci as risk variants for anterior cruciate ligament rupture," PLoS ONE. Apr. 2017. 12(4):e0173810.
Baker et al. "Genome-wide association studies and genetic testing: understanding the science, success, and future of a rapidly developing field," J Am Vet Med Assoc. Nov. 2019. 255(10): 1126-1136.
Broad Institute, SNP BICF2P262094. available via URL: <broadinstitute.org/files/shared/mammals/dog/snp2/snp_lists/chr6_allsnps.txt>, printed on Sep. 21, 2021.
Christopher C Chang, Carson C Chow, Laurent Cam Tellier, Shashaank Vattikuti, Shaun M Purcell and James J Lee (2015) "Second-generation PLINK: rising to the challenge of larger and richer datasets," *GigaScience* 4:7 (DOI: 10.1186/s13742-015-0047-8).
Cohen et al. "Quality Control Measures and Validation in Gene Association Studies: Lessons for Acute Illness," Shock. Mar. 2020. 53(3): 256-268.
Ekenstedt et al. "An *ARHGEF10* Deletion is Highly Associated with a Juvenile-Onset Inherited Polyneuropathy in Leonberger and Saint Bernard Dogs," PLoS Genetics. Oct. 2014. 10(10) e1004635.
Hattersley et al. "What makes a good genetic association study?," The Lancet. 2005. 366: 1315-1323.
Hirschhorn et al. "A comprehensive review of genetic association studies," Genetics in Medicine. vol. 4, No. 2, pp. 45-61, Mar. 2002.
Karlsson et al. (2013). Genome-wide analyses implicate 33 loci in heritable dog osteosarcoma, including regulatory variants near CDKN2AJB. Genome Biology. 14:R132.
Karlsson EK and Lindblad-Toh K., (2008) Leader of the Pack: gene mapping in dogs and other model organisms, Nature Revies/ Genetics, vol. 9, 713- 725.
Lindblad-Toh K, Wade CM, Mikkelsen TS, Karlsson EK, Jaffe DB, Kamal M, et al. (2005) Genome sequence, comparative analysis, and haplotype structure of the domestic dog. *Nature*, 438:803-819.
O'brien JA, Harvey CE, Kelly AM, Tucker JA. (1973) Neurogenic atrophy of the laryngeal muscles of the dog. *J Small Anim Pract* 14(9):521-32.
Rausch T, Zichner T, Schlattl A, Stutz AM, Benes V, Korbel JO, (2012) DELLY: structural variant discovery by integrated paired-end and split-read analysis. *Bioinformatics* 28:i333-9.
Safra et al. "Expanded dog leukocyte antigen (DLA) single nucleotide polymorphism (SNP) genotyping reveals spurious class II associations," The Veterinary Journal (2011). 189: 220-225.
Shaun Purcell, Benjamin Neale, Kathe Todd-Brown, Lori Thomas, Manuel A.R. Ferreira, David Bender, Julian Maller, Pamela Sklar, Paul I. W. De Bakker, Mark J. Daly, and Pak C. Sham (2007) "PLINK: A Tool Set for Whole-Genome Association and Population-Based Linkage Analyses," *Am J Hum Genet*. 81(3):559-575 (published online Jul. 25, 2007 (DOI: 10.1086/519795).

(Continued)

*Primary Examiner* — Carla J Myers
(74) *Attorney, Agent, or Firm* — Joseph T. Leone; DeWitt LLP

(57) ABSTRACT

Methods for diagnosing propensity to exhibit acquired peripheral neuropathy in dogs are described. The methods and kits test dogs for presence of a disease-associated genomic variant. Presence of the genomic variant indicates an increased likelihood of the dog developing an acquired peripheral neuropathy. This information can be used to guide preemptive clinical treatment of the animal for peripheral neuropathy and to choose dogs for selective breeding programs.

5 Claims, 5 Drawing Sheets

(56) References Cited

OTHER PUBLICATIONS

Xiang Zhou and Matthew Stephens (2012) "Genome-wide efficient mixed-model analysis for association studies," *Nature Genetics* 44:821-824.

Xiang Zhou and Matthew Stephens (2014) "Efficient multivariate linear mixed model algorithms for genome-wide association studies," *Nature Methods* 11(4):407-409.

Xiang Zhou, Peter Carbonetto and Matthew Stephens (2013) "Polygenic modeling with Bayesian sparse linear mixed models," *PLoS Genetics* 9(2):e1003264.

Xiang Zhou (2016) "A unified framework for variance component estimation with summary statistics in genome-wide association studies," *bioRxiv*. 042846 (http://biorxiv.org/content/early/2016/03/08/042846; a preprint server hosted by the Cold Spring Harbor Laboratory, Cold Spring Harbor, NY).

\* cited by examiner

GENETIC TESTING FOR INHERITED PERIPHERAL NEUROPATHY

CROSS-REFERENCE TO RELATED APPLICATIONS

This is a divisional of co-pending application Ser. No. 16/745,608, filed 17 Jan. 2020, which claims priority to provisional application Ser. No. 62/794,750, filed 21 Jan. 2019, which are incorporated herein by reference.

FEDERAL FUNDING STATEMENT

This invention was made with government support under OD019743 awarded by the National Institutes of Health. The government has certain rights in the invention

BACKGROUND

Peripheral neuropathies are a heterogeneous group of diseases that cause pathologic degeneration of the peripheral nervous system, and may involve motor, sensory and autonomic fiber types. Damage to peripheral nerves has several etiologies, including systemic disease such as diabetes and hypothyroidism, toxin exposures, nutritional deficiencies, infections and hereditary disorders. Neuropathy is also a feature of the aging process.

The most common inherited peripheral neuropathy in humans, Charcot-Marie-Tooth (CMT) disease, causes progressive deterioration of motor and sensory nerves, muscular atrophy, and chronic pain. About 1 in 2,500 individuals are affected by CMT. Current treatments for CMT manage symptoms rather than modify the disease course. CMT results in axonal degeneration in nerves with long axons, such that the neuropathy is generally more pronounced distally. Differentiation of various neuropathies is dependent on patient history, exclusion of metabolic disease, electro-diagnostics and genetic testing. In humans, CMT variants include CMT type 1 (CMT1) and CMT type 2 (CMT2). CMT1 variants are de- or dysmyelinating, while CMT2 variants are axonal neuropathies. In humans, over 80 causative genetic variants associate with CMT, although the genetic cause for many cases remains unknown. CMT1 is associated with mutations in genes that encode proteins influencing Schwann cell function and myelination. CMT2-associated genes are associated with critical axonal processes such as mitochondrial dynamics.

Idiopathic acquired laryngeal paralysis in the dog was first identified in the mid-1950s. (O'Brien J A, Harvey C E, Kelly A M, Tucker J A. Neurogenic atrophy of the laryngeal muscles of the dog. J Small Anim Pract 1973; 14(9):521-32.) Today it is a well-recognized specific clinical syndrome confirmed as a generalized acquired peripheral neuropathy (APN) condition with high prevalence in specific dog breeds. Clinically and diagnostically, APN resembles human CMT disease with associated alterations in electro-diagnostic profiles and pathologic changes to peripheral nerves. Although rare, CMT disease symptoms in humans can include laryngeal paralysis. Many canine diseases are caused by mutations in the same genes that produce corresponding disease in humans, including complex traits, such as hip dysplasia, and monogenic traits, such as muscular dystrophy.

A major barrier to rapid progress in the development of disease-modifying medical treatment for human patients affected with peripheral neuropathy is a lack of understanding of the genetic basis of the disease and the lack of suitable large animal models. Continued existence of this barrier represents an important problem because, currently, therapies for patients with peripheral neuropathy and other types of motor neuron disease such as amyotrophic lateral sclerosis (ALS) and CMT are entirely symptomatic and do not modify or reverse progression of the disease over time.

In certain dog breeds, acquired peripheral neuropathy (APN) syndrome, also referred to as late-onset peripheral neuropathy (LPN) is common. Labrador Retrievers represent >70% of APN/LPN cases, although other breeds can also be affected, particularly Golden Retrievers, Poodles, and Irish Setters. It is estimated that as many as 50-75% of Labrador Retrievers get APN when over 12 years of age. The Labrador Retriever is the most common dog breed in the USA. Affected dogs have often been used for breeding before clinical signs develop. There is currently no disease modifying therapy available for dogs with APN. Moreover, presentation of APN in the dog is similar to both ALS and CMT diseases in humans. Humans with CMT can develop upper airway disorders, and fast-course ALS patients may present with laryngeal paralysis. Thus, there is are long-felt and unmet needs for a large animal model of peripheral neuropathy, and a screening test to help identify at risk dogs and genetic carriers in the pet population.

SUMMARY

Disclosed herein is a method of selective breeding in dogs. The method comprises testing the genomic DNA of dogs for the presence of a disease associated genomic variant located in a genomic interval selected from:
  (i) about 16 Mb upstream or downstream of locus 7884602 on chromosome 21 (CFA21), and/or
  (ii) about 16 Mb upstream or downstream of locus 64357249 on chromosome 6 (CFA6), and/or
  (iii) about 16 Mb upstream or downstream of locus 61344357 on chromosome 13 (CFA13).

The presence of a SNP within any or all of these genomic intervals indicates an increased likelihood that the tested dogs and the tested dogs' offspring will develop an acquired or late-onset peripheral neuropathy at some point during their lifetimes.

This information is then used to breed the dogs selectively—that is, breeding only those dogs that test negative for the presence of a genomic variant within either or both of the genomic intervals.

The method can be refined to test the genomic DNA of the dogs for the presence of the single-nucleotide polymorphism within about 10 Mb, or within about 5 Mb upstream or downstream of locus 7884602 on CFA21 and/or locus 64357249 on CFA6 and/or locus 61344357 on CFA13. The genomic DNA of the dogs may also or alternatively be tested for presence of a causal genetic variant located within the FATS gene or the MTMR2 gene on CFA21.

More specifically still, the genomic DNA of the dogs can either be probed using at least one oligonucleotide probe dimensioned and configured to bind selectively to a SNP that is associated with a genomic variant in the regions of interest, or a PCR test can be undertaken to identify a genomic variant. Binding of the probe(s) indicates presence of a disease associated SNP in the genomic DNA of the dog in the genomic interval (and thus indicates a statistically significantly higher likelihood of the dog and the dog's offspring exhibiting an acquired or late-onset peripheral neuropathy).

Also disclosed herein is a corresponding method of pre-emptive clinical management of acquired peripheral neuropathy in dogs. In the same fashion as noted above, the method comprises testing the genomic DNA of dogs for the presence of a genomic variant located in a genomic interval selected from:
(i) about 16 Mb upstream or downstream of locus 7884602 on CFA21, and/or
(ii) about 16 Mb upstream or downstream of locus 64357249 on CFA6, and/or
(iii) about 16 Mb upstream or downstream of locus 61344357 on CFA13.

The presence of a SNP within any of the genomic intervals indicates an increased likelihood of the dogs and the dogs' offspring developing an acquired or late-onset peripheral neuropathy during their lifetimes.

Armed with that data, the dogs that test positive are then preemptively supplied peripheral neuropathy treatment to ameliorate, attenuate, or otherwise inhibit the onset of the peripheral neuropathy.

Figure 1:
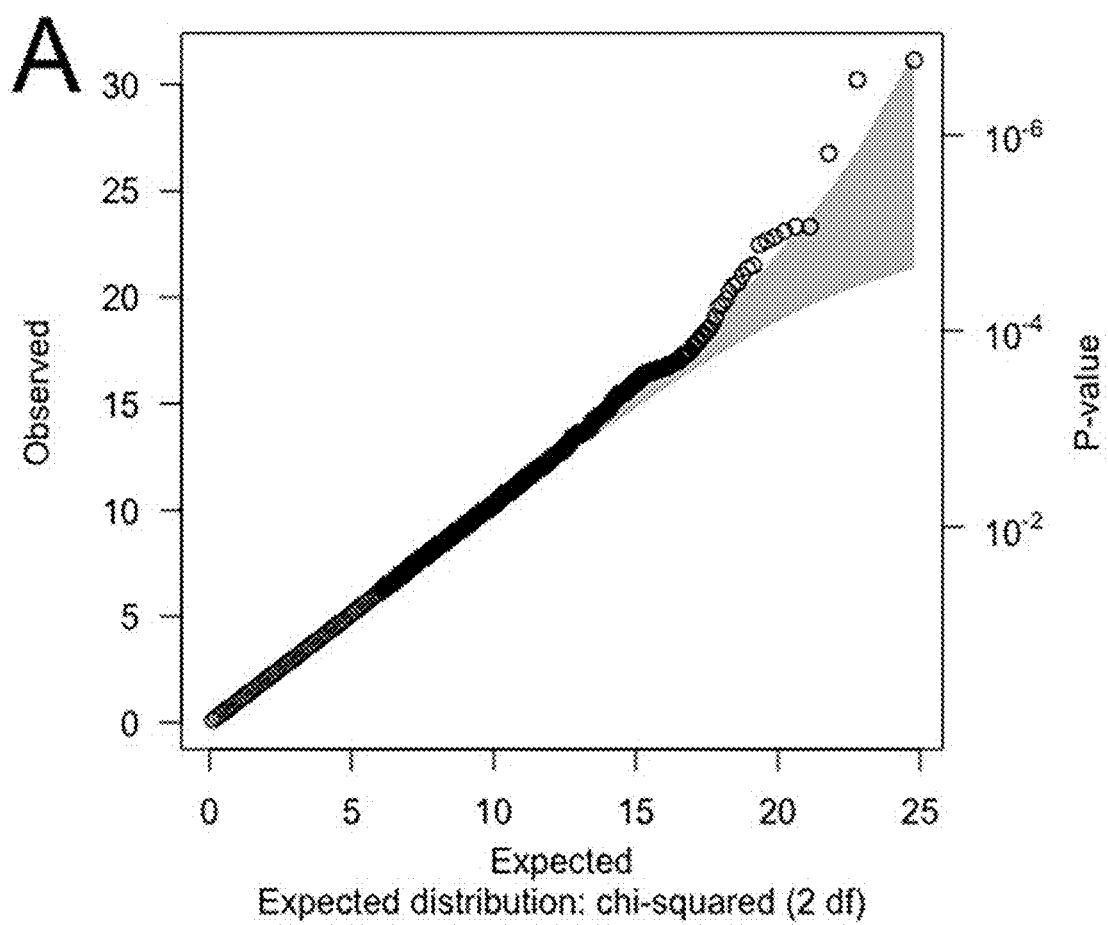
FIG. 1 is a quantile-quantile (QQ) plot of data from a GWAS of Labrador Retriever late-onset peripheral neuropathy (LPN). The QQ plot suggests genomic inflation is corrected by the linear mixed model (LMM), as the observed P-values (black circles) from the LMM follow the grey area of the empirical confidence intervals.
Figure 2:
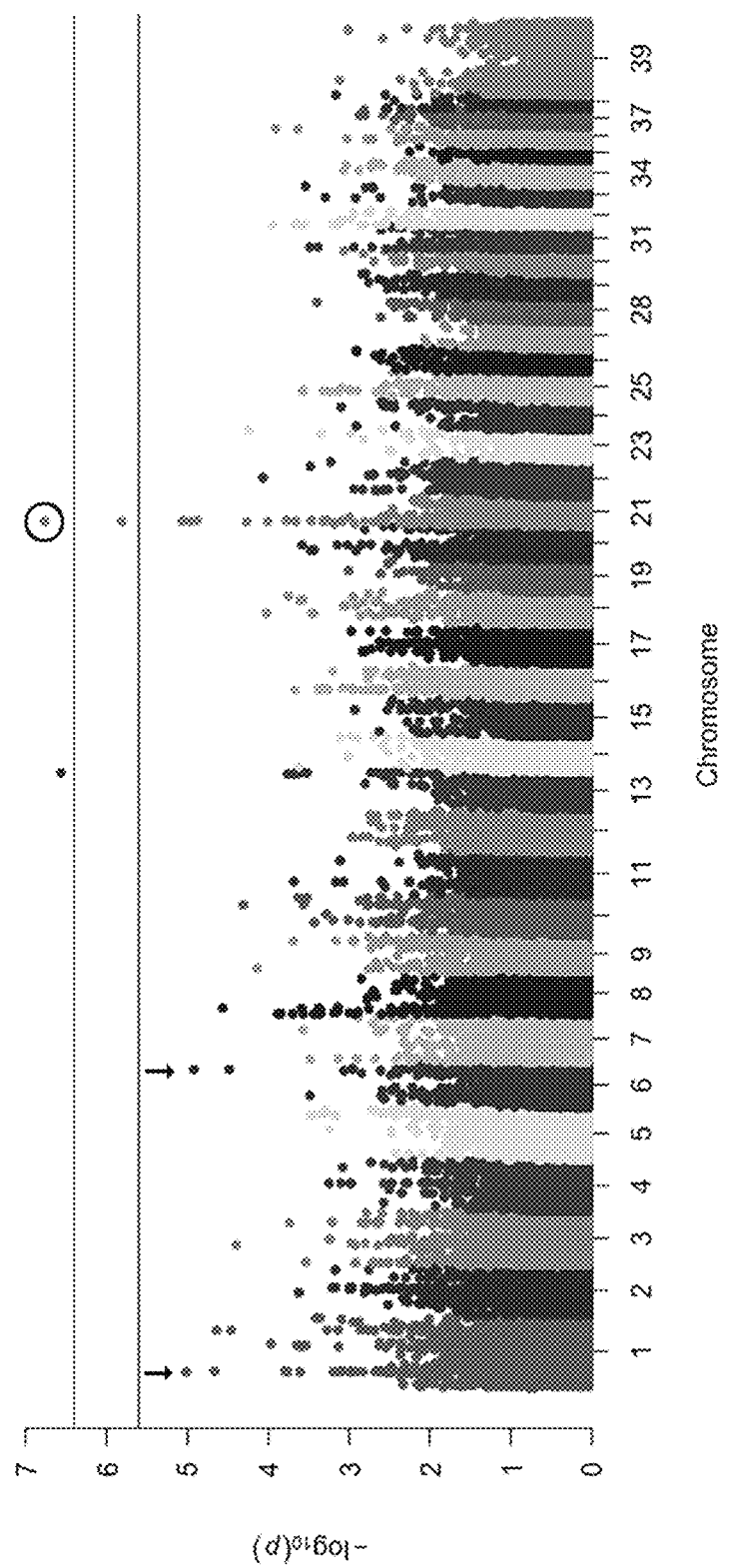
FIG. 2 is a Manhattan plot of the data presented in FIG. 1. The X-axis displays the genomic coordinates by chromosome number. The Y-axis displays the negative logarithm of the association P-value for each single nucleotide polymorphism (SNP) displayed on the X-axis; each dot on the Manhattan plot signifies a SNP. Because the strongest associations have the smallest P values (e.g., $10^{-5}$), their negative logarithms have the greatest values (e.g., 5) on the Y-axis in the corresponding Manhattan plot. A SNP on chromosome 21 (black circle) has the lowest P value ($1.72 \times 10^{-7}$) and is part of a cluster. SNPs on chromosomes 1, 6 and 13 (black arrows) are also of interest due to their proximity to genes associated with neurodegeneration.

The data in FIGS. 1 and 2 were derived from 98 cases and 48 controls using the Illumina CanineHD-brand Genotyping BeadChip. Analysis was performed using GEMMA. A Bonferroni correction for SNP number and haplotype block number revealed $P<3.68\times10^{-7}$ and $P<3.68\times10^{-6}$, respectively.

Figure 3:
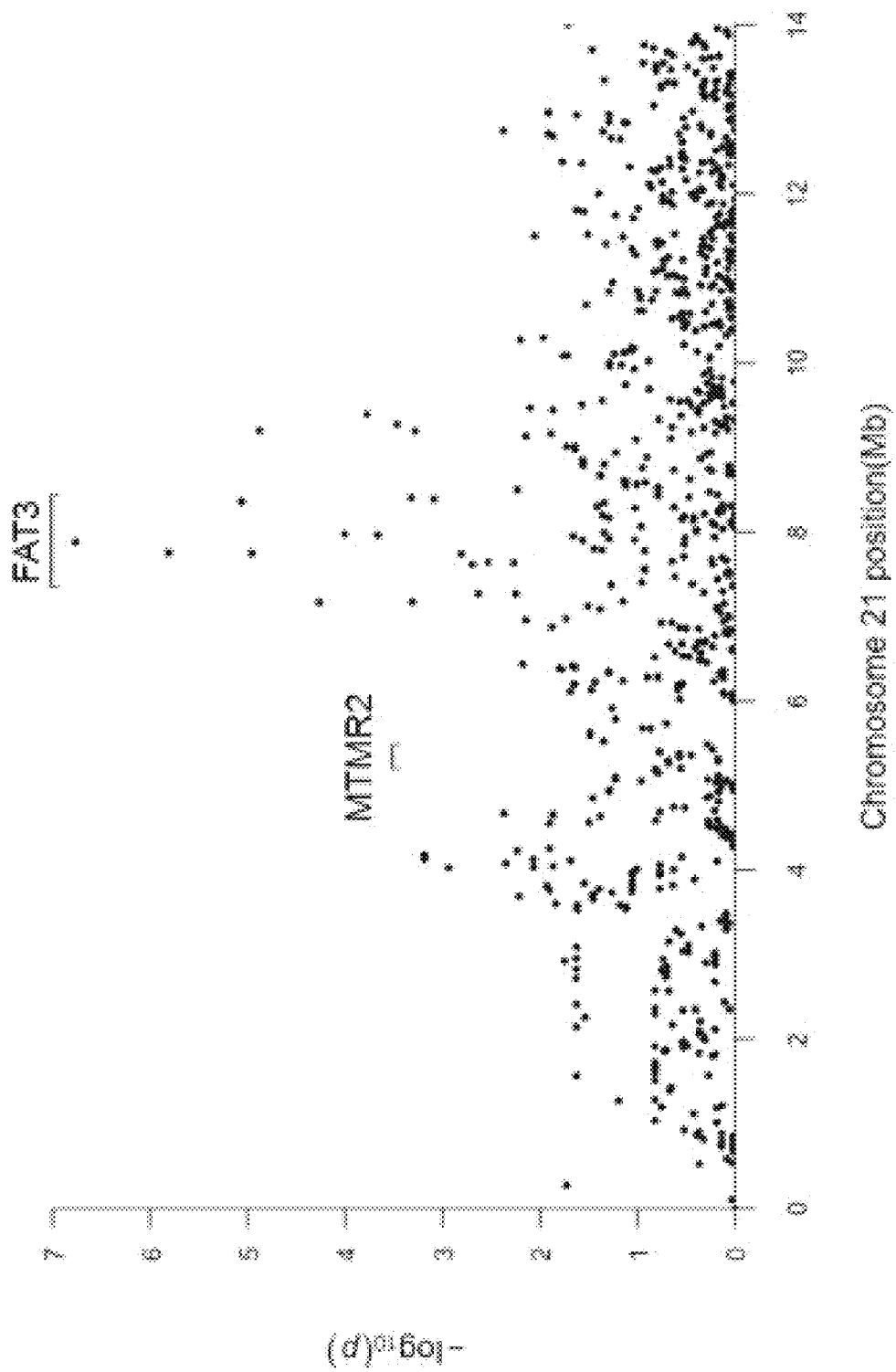

FIG. 3 is a Manhattan plot of chromosome 21 from a GWAS of Labrador Retriever late-onset peripheral neuropathy (LPN). Two peaks are present. Associated SNPs, located at ~7.7 Mb, reside within FAT3, while MTMR2, which is associated with CMT type 4B1, is flanked by peaks of interest. This mapping is based on the Boxer reference genome CanFam3.1. The top SNPs from these peaks are in moderate linkage disequilibrium (r2>0.5). The locations of FAT3 and MTMR2 are labeled.

Figure 4:
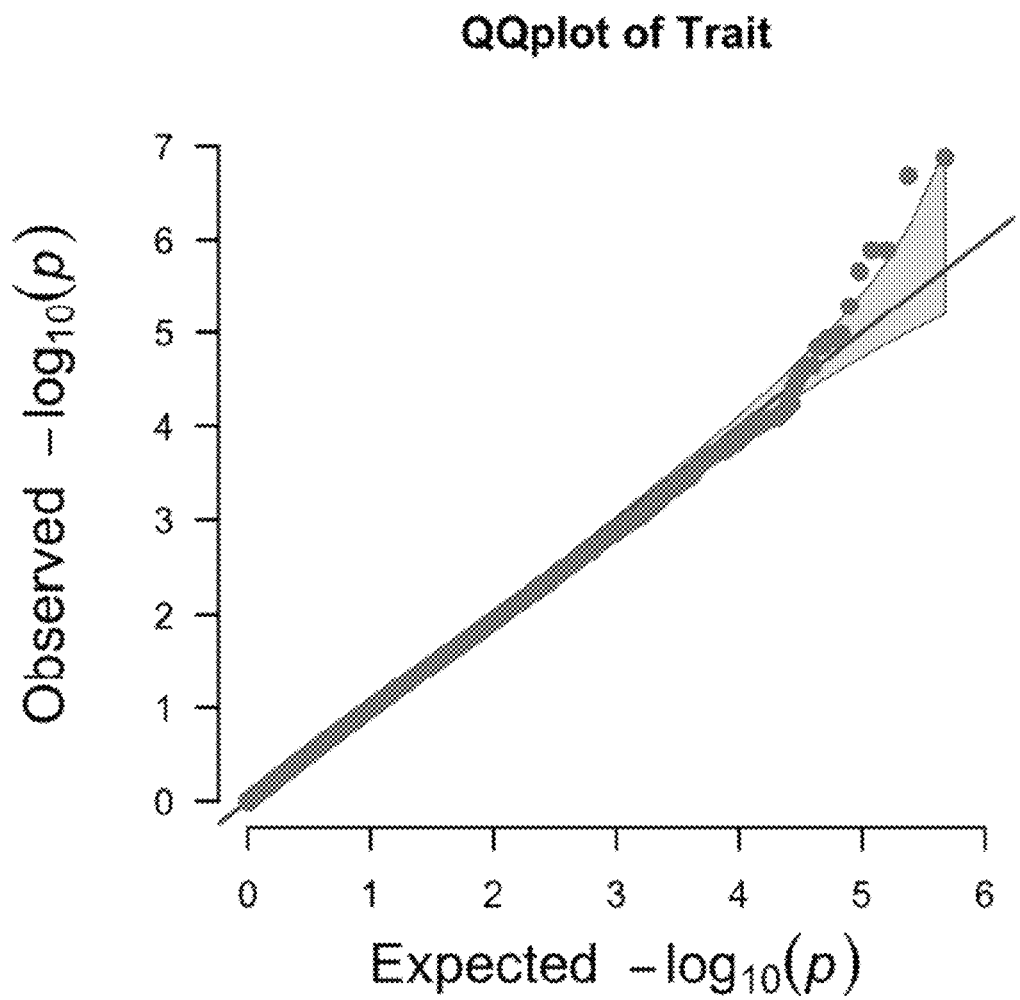

FIG. 4 is a quantile-quantile (QQ) plot of data from an updated GWAS of Labrador Retriever late-onset peripheral neuropathy (LPN). The QQ plot suggests genomic inflation is corrected by the linear mixed model (LMM), as the observed P-values (circles) from the LMM follow the grey area of the empirical confidence intervals.

Figure 5:
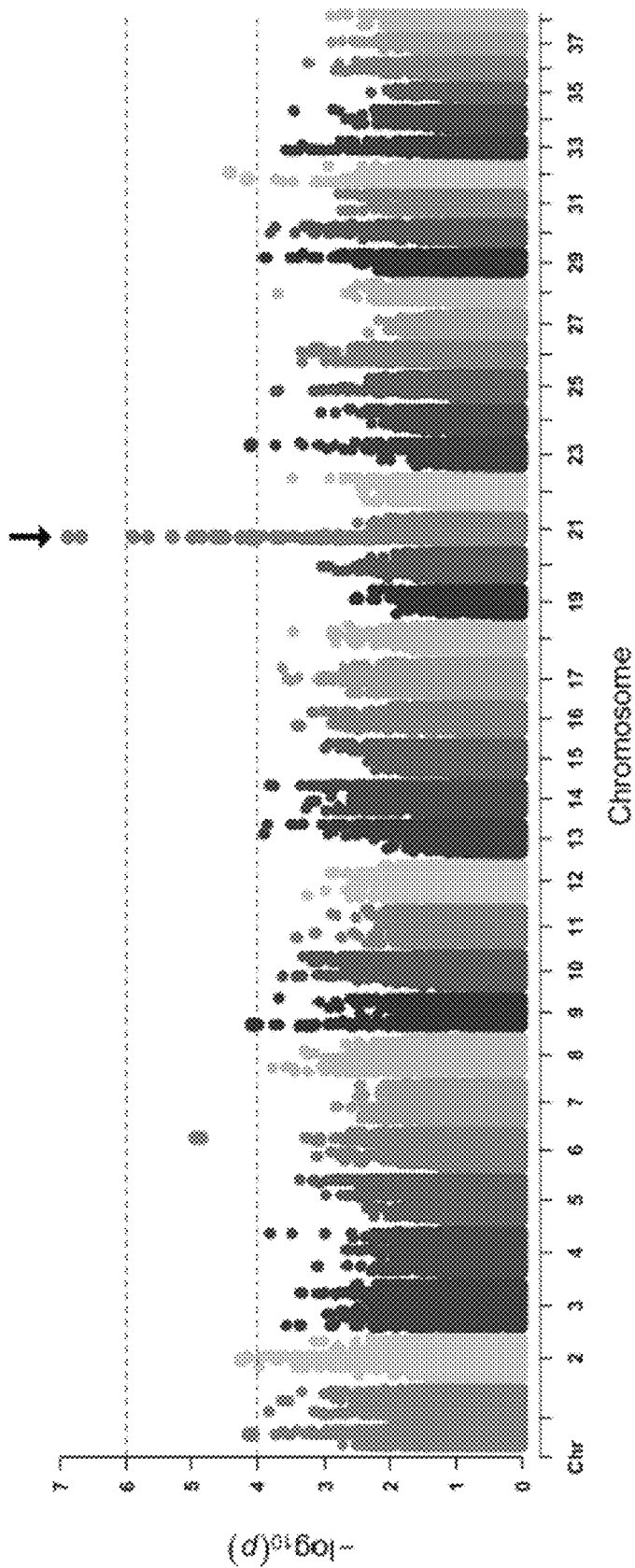

FIG. 5 is a Manhattan plot of the data presented in FIG. 4. Analysis was undertaken using the "Gaston" software package. (Hervé Perdry, Claire Dandine-Roulland, Deepak Bandyopadhyay, and Lutz Kettner (Apr. 2, 2019). The Gaston software is freeware available online from "The R Project for Statistical Computing" at CRAN.R-project.org/package=gaston. It is maintained online by Hervé Perdry of L'Université Paris-Sud, Orsay, France.). The Y-axis displays the negative logarithm of the association P-value for each single nucleotide polymorphism (SNP) displayed on the X-axis; each dot on the Manhattan plot signifies a SNP. Because the strongest associations have the smallest P values (e.g., $10^{-5}$), their negative logarithms have the greatest values (e.g., 5) on the Y-axis in the corresponding Manhattan plot. The SNP on chromosome 21 (black arrow) has the lowest P value ($1.28 \times 10^{-7}$).

DETAILED DESCRIPTION

Abbreviations and Definitions

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. Unless otherwise stated, the indefinite articles "a" and "an" mean "one or more." When referring to a previously stated element, the definite article "the" does not limit the stated definition of "a" and "an," as meaning "one or more."

All combinations of method or process steps as used herein can be performed in any order, unless otherwise specified or clearly implied to the contrary by the context in which the referenced combination is made.

The methods and kits disclosed herein can comprise, consist of, or consist essentially of the essential elements and limitations described herein, as well as any additional or optional steps, ingredients, components, or limitations described herein or otherwise useful in gathering, preparing, and sequencing genomic DNA for analysis.

APN=Acquired peripheral neuropathy. This term is used synonymously herein with LPN=late-onset peripheral neuropathy.

CMT=Charcot-Marie-Tooth (CMT) disease.

GEMMA: Genome-wide efficient mixed model association. GEMMA is a free, open-source whole genome association analysis program that performs a range of large-scale genomic analyses in a computationally efficient manner. It is available online from the website of Professor Xiang Zhou of the University of Michigan, School of Public Health, Department of Biostatistics School of Public Health, Ann Arbor, Michigan See xzlab.org/software.html. GEMMA is the software used to implement the Genome-wide Efficient Mixed Model Association algorithm for a standard linear mixed model and some of its close relatives for genome-wide association studies (GWAS). It fits a univariate linear mixed model (LMM) for marker association tests with a single phenotype to account for population stratification and sample structure, and for estimating the proportion of variance in phenotypes explained (PVE) by typed genotypes ("chip heritability"). It fits a multivariate linear mixed model (mvLMM) for testing marker associations with multiple phenotypes simultaneously while controlling for population stratification, and for estimating genetic correlations among complex phenotypes. It fits a Bayesian sparse linear mixed model (BSLMM) using Markov chain Monte Carlo (MCMC) for estimating PVE by typed genotypes, predicting phenotypes, and identifying associated markers by jointly modeling all markers while controlling for population structure. It estimates variance component/chip heritability, and partitions it by different SNP functional categories. In particular, it uses a Haseman Elston regression or restricted maximum likelihood (REML) artificial intelligence algorithm to estimate variance components when individual-level data are available. It is computationally efficient for large scale GWAS and uses freely available open-source numerical libraries. It is distributed under the GNU General Public License. See Xiang Zhou and Matthew Stephens (2012) "Genome-wide efficient mixed-model analysis for association studies," *Nature Genetics* 44: 821-824; Xiang Zhou and Matthew Stephens (2014) "Efficient multivariate linear mixed model algorithms for genome-wide association studies," *Nature Methods* 11(4): 407-409; Xiang Zhou, Peter Carbonetto and Matthew Stephens (2013) "Polygenic modeling with Bayesian sparse linear mixed models," *PLoS Genetics* 9(2): e1003264; and Xiang Zhou (2016) "A unified framework for variance component estimation with summary statistics in genome-wide association studies," *bioRxiv.* 042846 (biorxiv.org/content/early/2016/03/08/042846; a preprint server hosted by the Cold Spring Harbor Laboratory, Cold Spring Harbor, NY).

GWAS: Genome-wide association study. A genome-wide association study is an analysis of genetic variation at specified loci in different individuals to see if any variant(s) is (are) associated with a phenotypic trait. As the name indicates, genetic markers across the complete genome of each individual test subject are tested to find genetic variations associated with a particular disease, in this case APN in dogs. Once new genetic associations are identified, the information is used to detect, treat and/or prevent the disease. Such studies are particularly useful in finding genetic variations that contribute to common, but complex diseases.

LD: Linkage disequilibrium. Linkage disequilibrium is the non-random association of alleles at two or more loci that descend from single, ancestral chromosomes.

MDS: multidimensional scaling.

MLM, LLM (synonymous): mixed linear model, linear mixed model, respectively.

PLINK: PLINK is a free, open-source whole genome association analysis program that performs a range of large-scale genomic analyses in a computationally efficient manner. The PLINK software was developed (and continues to be refined) by Shaun Purcell, Christopher Chang, and others at the Center for Human Genetic Research, Massachusetts General Hospital, and the Broad Institute of Harvard and M.I.T., as well as Stanford University's Department of Biomedical Data Science. PLINK v.1.9 is available online as of May 19, 2017, at cog-genomics.org/plink/1.9/. Plink v. 2.0 was released May 9, 2017, and is available online at cog-genomics.org/plink/2.0/. See Christopher C Chang, Carson C Chow, Laurent CAM Tellier, Shashaank Vattikuti, Shaun M Purcell and James J Lee (2015) "Second-generation PLINK: rising to the challenge of larger and richer datasets," *GigaScience* 4:7 (DOI: 10.1186/s13742-015-0047-8) and Shaun Purcell, Benjamin Neale, Kathe Todd-Brown, Lori Thomas, Manuel A. R. Ferreira, David Bender, Julian Maller, Pamela Sklar, Paul I. W. de Bakker, Mark J. Daly, and Pak C. Sham (2007) "PLINK: A Tool Set for Whole-Genome Association and Population-Based Linkage Analyses," *Am J Hum Genet.* 81(3): 559-575 (published online Jul. 25, 2007 (DOI: 10.1086/519795).

SNP: Single nucleotide polymorphism.

Unless otherwise noted, technical terms are used according to conventional usage. Definitions of common terms in genetics, genomics, and molecular biology may be found in Benjamin Lewin, "Genes V," published by Oxford University Press, 1994 (ISBN 0-19-854287-9) and Kendrew et al. (eds.), "The Encyclopedia of Molecular Biology," published by Blackwell Science Ltd., 1994 (ISBN 0-632-02182-9).

Genome-Wide Association Study:

Two genome-wide association studies were conducted using populations of Labrador Retrievers. The first GWAS used a population of 56 cases and 26 controls. This first study showed that a single nucleotide polymorphism (SNP) on CFA1 tags the causal variant for APN in mammals generally, dogs particularly, and Labrador Retrievers most specifically. This SNP (TIGRP2P18586_rs8746233) is located at 29193391 on CFA1, is associated with APN (P=5.00E-7), and is located in a region of numerous genes associated with neuronal regulation. Permutation testing indicates that this P value meets genome-wide significance. The SNP is not in strong linkage disequilibrium with any other SNP on the Illumina SNP Array, indicating that the causal variant lies within a 16 Mb interval, between 24 Mb and 40 Mb on CanFam2.1. The first GWAS was done using a linear mixed model with GEMMA that accounts for population stratification. Genomic-wide significance was calculated from the 5% quantile of the population of minimum P values from 10,000 GWAS permutations with randomly permuted phenotypes.

Importantly, model-based tests suggest that the associated SNP on CFA1, which is a marker for the causal variant, is inherited in an autosomal dominant fashion in the Labrador Retriever, as is the case with familial ALS and many forms of CMT in humans. See Table 1.

TABLE 1

Distribution of LPN phenotypes and genotypes, CFA1

|  | GG | GA | AA |
|---|---|---|---|
| Case | 15 | 30 | 11 |
| Control | 0 | 5 | 21 |

In Labrador Retrievers, the major allele for this SNP is G and the minor allele is A. The GG genotype indicates that even SNP-based genetic testing of Labrador Retrievers has commercial value in the veterinary market for genetic testing for selective breeding and preemptive clinical management of affected dogs.

A second, larger GWAS of APN/LPN in the Labrador Retriever, using dogs recruited from throughout the United States and Canada was also performed. The dogs studied were phenotyped for the APN/LPN condition by a board-certified veterinary surgeon or neurologist. This study revealed that a SNP on CFA21 is significantly associated with development of LPN in the Labrador Retriever. This SNP (BICF2P117167) is located at 7884602 on CFA21 (canFam3.1 reference), and is strongly associated with LPN (P=5.34×10$^{-7}$). Genome-wide significance, determined using a Bonferroni correction for SNP number, is P<3.68× 10$^{-7}$. Detailed evaluation of this region reveals 2 SNP peaks, located about 3.5 million base pairs apart. See FIG. 3. These peaks are in linkage disequilibrium. The relatively large physical separation between these regions may reflect the presence of a large structural variant.

The most significant SNP from this GWAS is located in the FAT3 gene. FAT3 expression is restricted to the nervous system. FAT3 has not been widely studied, but interest has focused on its effects on retinal innervation. Myotubularin-related protein 2 (MTMR2) is another strong candidate gene within the chromosome 21 locus. Loss of function in MTMR2 is responsible for CMT Type 4B1. Interestingly, this CMT subtype is one of a few that results in laryngeal paralysis in humans. This locus of interest on chromosome 21 thus spans from 3,200,000 base pairs to 10,500,000 base pairs.

SNPs on chromosomes 1, 6 and 13 are also of interest with regards to their association with the LPN condition. The SNP on CFA 13 is also of interest because of its location in the ADAMTS3 gene. This gene is a member of a family of genes that has been associated with ALS in humans.

The second GWAS study of LPN in the Labrador Retriever used only dogs that were phenotyped by either a board-certified veterinary neurologist or surgeon. This GWAS contains 63 cases and 23 controls. The SNP significantly associated with LPN using this group of dogs (BICF2P262094) is located on CFA 6 at 64357249. See FIG. 2 (canFam3.1 reference). This SNP is in the region of a number of genes that are associated with the nervous system in people. Overall, the region on CFA 6 that is of interest, based on both GWA studies, spans from 61,000,000-66,000,000 base pairs.

Similarly, the region on chromosome 1 that associates with LPN in the Labrador, based on the results of these GWAS, spans 25,000,000-27,000,000 base pairs.

Importantly, the genotype-phenotype tables associated with the SNPs on CFA21 and CFA6 both suggest LPN is inherited in an autosomal dominant fashion in the Labrador Retriever (Tables 2 and 3).

TABLE 2

Distribution of LPN phenotypes and genotypes, CFA21

|  | Homozygous AA | Heterozygous AG | Homozygous GG | Total |
|---|---|---|---|---|
| Case | 27 | 47 | 24 | 98 |
| Control | 0 | 14 | 34 | 48 |
| Total | 27 | 61 | 58 | 146 |

For the top associated SNP on chromosome 21, all homozygous AA dogs and 77% of AG heterozygote dogs have phenotypic evidence of a LPN. Assuming a LPN is an autosomal dominant disease, the odds ratio for disease development, based on this SNP, is 7.5.

TABLE 3

Distribution of LPN phenotypes and genotypes, CFA6

|  | Homozygous GG | Heterozygous GA | Homozygous AA | Total |
|---|---|---|---|---|
| Case | 46 | 34 | 18 | 98 |
| Control | 6 | 24 | 18 | 48 |
| Total | 52 | 58 | 36 | 146 |

A SNP or PCR-based genetic test of Labrador Retrievers has substantial commercial value in the veterinary market for selective breeding, diagnosing, and preemptive clinical managing of affected dogs. There is a great interest in a genetic test for this condition amongst veterinarians, and Labrador Retriever owners and breeders, as this is a very common disease in Labrador Retrievers with high morbidity.

Updated Genome-Wide Association Study:

An updated GWAS of APN/LPN in the Labrador Retriever, using additional dogs recruited from throughout the United States and Canada was also performed. This data set included the analyses of the 146 dogs reported in Tables 2 and 3, and an additional 25 dogs (for a total of 171 individuals). The dogs were phenotyped for the APN/LPN condition by a veterinarian. This third study again revealed that a SNP on CFA21 is significantly associated with development of LPN in the Labrador Retriever. This SNP (BICF2P117167) is located at 7884602 on CFA21 (canFam3.1 reference), and is strongly associated with LPN. See FIGS. 4 and 5.

FIG. 4 is a quantile-quantile (QQ) plot of data from the updated GWAS of Labrador Retriever late-onset peripheral neuropathy (LPN). FIG. 5 is a Manhattan plot of the data presented in FIG. 4. The Y-axis displays the negative logarithm of the association P-value for each single nucleotide polymorphism (SNP) displayed on the X-axis; each dot on the Manhattan plot signifies a SNP. Because the strongest associations have the smallest P values (e.g., $10^{-5}$), their negative logarithms have the greatest values (e.g., 5) on the Y-axis in the corresponding Manhattan plot. The SNP on chromosome 21 (black arrow) has the lowest P value ($1.28 \times 10^{-7}$).

The data in FIGS. 4 and 5 were derived from 120 cases and 51 controls using the Illumina CanineHD-brand Genotyping BeadChip imputed to the 770K ThermoFisher Axiom-brand Canine Genotyping Array (ThermoFisher Scientific, Waltham, MA, USA; catalog no. 550869). The Axiom-brand Canine HD Array was developed by screening over 2000 samples using the Axiom-brand Canine Genotyping Array Sets A and B. The samples covered over 50 breeds and were carefully selected with appropriate pedigree to maximize polymorphic content. The array offers over 710,000 markers for validation and discovery of variants associated with specific phenotypes. The content on the array was aligned with the CanFam3 reference genome.

Statistical analysis of the results was performed using the Gaston software, as noted previously. For this analysis, two commonly utilized cut-off threshold lines at p-value $1 \times 10^{-6}$ and $1 \times 10^{-4}$ were used.

TABLE 4

Updated Distribution of LPN phenotypes and genotypes, CFA21

|  | Homozygous (AA) | Heterozygous (AG) | Homozygous (GG) | Total |
|---|---|---|---|---|
| Case | 36 | 54 | 30 | 120 |
| Control | 0 | 16 | 35 | 51 |
| Total | 36 | 70 | 65 | 171 |

Canine Samples and Phenotyping:

DNA was isolated from client-owned Labrador Retrievers using blood or buccal swabs. A four-generation pedigree was collected from each dog to ensure purebred status and identify siblings, which were excluded from the GWAS.

Genome-Wide Association:

Genome-wide SNP genotyping was performed using the Illumina CanineHD BeadChip, which genotypes 173,662

SNPs evenly spaced across the genome. Data underwent quality control filtering using PLINK [Chang C C, Chow C C, Tellier L C A M, Vattikuti S, Purcell S M, Lee J J. Second-generation PLINK: rising to the challenge of larger and richer datasets. GigaScience. 2015; 4:7]. All samples had a genotyping call rate of ≥95%. SNPs were excluded if the minor allele frequency (MAF) was ≤0.05; SNPs were also excluded if the genotyping rate was ≤95%). SNPs were also excluded if they deviated from Hardy-Weinberg equilibrium at P<1E-07.

To account for ancestral population structure and family relatedness in the study dogs, single marker linear mixed model (LMM) analysis was performed using GEMMA (Genome-wide Efficient Mixed Model Association) [Zhou X, Stephens M. Genome-wide efficient mixed-model analysis for association studies. Nat Genet. 2012; 44: 821-824], a software tool optimized for complex trait GWAS.

Genome-Wide Significance:

Genome-wide significance was defined using permutation testing. Use of a Bonferroni correction for the number of SNPs tested is sometimes too conservative in dog breeds, as extensive LD means that SNPs are often inherited in haplotype blocks [Lindblad-Toh K, Wade C M, Mikkelsen T S, Karlsson E K, Jaffe D B, Kamal M, et al. Genome sequence, comparative analysis, and haplotype structure of the domestic dog. Nature. 2005; 438: 803-819]. Genome-wide significance was defined by randomly permuting the phenotypes and re-running the GWAS LMM 10,000 times. Genome-wide significance was defined by identifying the 5% quantile of the set of minimum P-values from the GWAS permutations. Additionally, we calculated the number of haplotype blocks in the Labrador Retriever SNP data using PLINK, using LD windows of 500 kb, 1 Mb, and 5 Mb and used the number of haplotype blocks to estimate genome-wide significance by Bonferroni correction of P<0.05.

Defining Associated Loci in the Genome:

After obtaining the results from the GEMMA LMM for the APN trait, LD-based clumping was calculated in PLINK to define the region of association with the APN trait from the GWAS results. LD clumping defined a candidate locus around the associated SNP. A region within ($r^2$>0.5, within 2 Mb of the associated SNP) was defined. These settings were modified from another GWAS for a complex trait in dogs. [Karlsson et al. (2013). Genome-wide analyses implicate 33 loci in heritable dog osteosarcoma, including regulatory variants near CDKN2A/B. *Genome Biology.* 14:R132.] These regions were then investigated with the NCBI Canine Genome Map Viewer to identify nearby genes using the CanFam 3.0 reference sequence.

Mode of Inheritance:

Model-based analysis of case and control genotypes was performed using PLINK. This suggested that the associated SNP on CFA1, which is a marker for the causal variant, is inherited in an autosomal dominant fashion in the Labrador Retriever, as is the case with familial ALS and many forms of CMT in people. In addition, a detailed pedigree tree is being constructed using four-generation pedigrees from each dog was used to evaluate the mode of inheritance and indicates an autosomal dominant inheritance pattern.

Fine Mapping:

Fine mapping should include the original GWAS breed and use of another breed sharing the phenotype, as haplotypes are commonly shared between breeds. A replicated/validated risk loci GWAS data set will be generated using Labrador and Golden Retriever SNPs. Fine-mapping association analysis will include a between-breed association design using both breeds (Karlsson & Lindblad-Toh 2008). Fine mapping will use the KASP™—brand genotyping (LGC Genomics, Beverly, MA) and a dense set of SNPs selected from breed-specific whole genome sequences High-Density De novo Assembly of the Labrador Genome and Whole-Genome Sequencing A de novo assembly of an aged Labrador Retriever that does not have evidence of APN will be constructed to provide an appropriate reference genome for further whole genome sequencing. DNA will be isolated from a blood sample or a saliva swab. dsDNA purity and concentration will be assessed. DNA from selected dogs will be submitted to the University of Wisconsin-Madison Biotechnology Center. A guided assembly of the Labrador Retriever genome. We will combine a target coverage to ~50× of long-read PacBio (Pacific Biosciences, Menlo Park, CA) reads and Oxford nanopore reads (Oxford Nanopore Technologies, Oxford, England). Chromosomal-level scaffolding with be undertaken with Hi-C (Illunina, San Diego, CA). The combination of long-read sequencing technologies and Hi-C will provide accurate assembly; additional nucleotide-level correction, if needed, would be achieved through consensus polishing using very high depth Illumina short-read sequencing. This work will create a high quality Labrador Retriever genome assembly and will enhance our ability to detect of structural and sequence variation.

Long-read sequencing of DNA from APN affected and unaffected dogs will then be undertaken using PacBio sequencing. These reads will be mapped to the aforementioned de novo assembly. Images will be analyzed using the standard Illumina Pipeline.

Variant Filtering: The resulting long-read sequences will be mapped to the de novo assembly created for the Labrador Retriever. Single nucleotide polymorphisms (SNPs) from dogs with both Canine HD Genotyping BeadChip (Illumina Inc, San Diego, CA) data and whole-genome sequencing data will be compared to assure the resulting genotypes are identical. All SNPs identified by the whole-genome sequencing data will subsequently be filtered for low genotype quality scores. An association analysis will be performed using PLINK with options specifying an additive model. The conservative Bonferroni correction method will be used to correct for multiple testing.

Structural Variant Analysis: We will utilize the DELLY program (Rausch T, Zichner T, Schlattl A, Stutz A M, Benes V, Korbel J O. DELLY: structural variant discovery by integrated paired-end and split-read analysis. Bioinformatics 2012; 28:i333-9) to evaluate the whole-genome sequence data for genomic structural variants that associate with disease phenotype in our region of interest. Variants including deletions, duplications, inversions and translocations will be accessed between cases and controls for Labrador and Golden Retrievers.

What is claimed is:

1. A method for breeding a Labrador Retriever, the method comprising:
 (a) isolating genomic DNA from a first Labrador Retriever;
 (b) assaying the genomic DNA of step (a) for presence of an A or G nucleotide at a single-nucleotide polymorphism (SNP) BICF2P117167 on CFA 21;
 (c) selecting the first Labrador Retriever having a GG genotype at the SNP of step (b) as indicative of a decreased likelihood of the first Labrador Retriever and the first Labrador Retriever's offspring developing an acquired peripheral neuropathy during their lifetimes; and then
 (d) breeding the first Labrador Retriever.

2. The method of claim 1, wherein step (b) comprises assaying the genomic DNA of the first Labrador Retriever for BICF2P117167 located within the FAT3 gene on CFA21.

3. The method of claim 1, wherein step (b) comprises:
 (i) contacting the genomic DNA with at least one oligonucleotide probe dimensioned and configured to bind selectively to the SNP or undertaking PCR testing for the SNP; and then
 ii) detecting whether any portion of the genomic DNA of the Labrador Retriever selectively binds to the oligonucleotide probe, wherein binding indicates presence of the SNP in the genomic DNA of the Labrador Retriever or detecting changes in PCR product that indicate the SNP in the genomic DNA of the Labrador Retriever.

4. A method for breeding a Labrador Retriever, the method comprising:
 (a) isolating genomic DNA from a first Labrador Retriever;
 (b) assaying the genomic DNA of step (a) for presence of an A or G nucleotide at a single-nucleotide polymorphism (SNP) BICF2P117167 on CFA 21,
by contacting the genomic DNA with at least one oligonucleotide probe dimensioned and configured to bind selectively to the SNP; and then detecting whether any portion of the genomic DNA of the Labrador Retriever selectively binds to the oligonucleotide probe, wherein binding indicates presence of the SNP in the genomic DNA of the first Labrador Retriever;
 (c) selecting the first Labrador Retriever having a GG genotype at the SNP of step (b) as indicative of a decreased likelihood of the first Labrador Retriever and the first Labrador Retriever's offspring developing an acquired peripheral neuropathy during their lifetimes; and then
 (d) breeding the first Labrador Retriever.

5. The method of claim 4, wherein step (b) comprises assaying the genomic DNA of step (a) for BICF2P117167 located within the FAT3 gene on CFA21.

* * * * *